United States Patent
Kostansek et al.

(10) Patent No.: US 6,762,153 B2
(45) Date of Patent: Jul. 13, 2004

(54) DELIVERY SYSTEM FOR CYCLOPROPENES

(75) Inventors: Edward Charles Kostansek, Buckingham, PA (US); Richard Martin Jacobson, Chalfont, PA (US); Leah Anne Weisel, Jamison, PA (US); Bridget Marie Stevens, Horsham, PA (US)

(73) Assignee: Rohm And Haas Company, Philadelphia, PA (US)

( * ) Notice: Subject to any disclaimer, the term of this patent is extended or adjusted under 35 U.S.C. 154(b) by 0 days.

(21) Appl. No.: 10/262,397

(22) Filed: Oct. 1, 2002

(65) Prior Publication Data

US 2003/0100450 A1 May 29, 2003

Related U.S. Application Data

(60) Provisional application No. 60/330,320, filed on Oct. 18, 2001.

(51) Int. Cl.[7] ........................ A01N 25/10; A01N 27/00
(52) U.S. Cl. ...................................... 504/357; 504/359
(58) Field of Search ................................. 504/357, 359

(56) References Cited

U.S. PATENT DOCUMENTS

| 5,518,988 A | 5/1996 | Sisler et al. ................. 504/114 |
| 6,017,849 A | 1/2000 | Daly et al. .................. 504/114 |
| 6,426,319 B1 | 7/2002 | Kostansek .................. 504/357 |
| 6,444,619 B1 | 9/2002 | Kostansek .................. 504/357 |

FOREIGN PATENT DOCUMENTS

| EP | 0565354 A1 | 10/1993 |
| WO | WO99/04765 | 2/1999 |
| WO | WO00 10386 A | 1/2000 |
| WO | WO02/24171 A1 | 3/2002 |

*Primary Examiner*—S. Mark Clardy
(74) *Attorney, Agent, or Firm*—Thomas D. Rogerson

(57) ABSTRACT

The present invention relates to complexes formed from molecular encapsulation agents such as cyclodextrin, and cyclopropene and its derivatives such as methylcyclopropene, which are capable of inhibiting the ethylene response in plants. More specifically this invention relates to compositions of cyclopropenes and molecular encapsulation agents containing additives to improve the release of the cyclopropene when the composition is contacted with water.

10 Claims, No Drawings

DELIVERY SYSTEM FOR CYCLOPROPENES

Cross Reference To Related Patent Applications

This is a non-provisional application of prior pending U.S. provisional application serial No. 60/330,320 filed Oct. 18, 2001.

The present invention relates to complexes formed from molecular encapsulation agents such as cyclodextrin, and cyclopropene and its derivatives such as methylcyclopropene, which are capable of inhibiting the ethylene response in plants. Such complexes provide a convenient means for storing and transporting these compounds which are reactive gases and highly unstable because of oxidation and other potential reactions. Such complexes also provide convenient methods of delivering to plants these compounds in order to extend their shelf life.

It is well known that ethylene can cause the premature death of plants including flowers, leaves, fruits and vegetables through binding with certain receptors in the plant. It can also promote leaf yellowing and stunted growth as well as premature fruit, flower and leaf drop. Because of these ethylene-induced problems, very active and intense research presently concerns the investigation of ways to prevent or reduce the deleterious effects of ethylene on plants. U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed. As a solution to these problems, U. S. Pat. No. 6,017,849 discloses a method of incorporating these gaseous compounds into a molecular encapsulation agent complex in order to stabilize their reactivity and thereby provide a convenient and safe means of storing, transporting and applying or delivering the active compounds to plants. For the most active cyclopropene derivative disclosed in U.S. Pat. No. 5,518,988, 1-methylcyclopropene, the preferred molecular encapsulation agent is a cyclodextrin with α-cyclodextrin being the most preferred. The application or delivery of these active compounds is then accomplished by simply adding water to the molecular encapsulation agent complex. The complex prepared according to the methods disclosed in U.S. Pat. No. 6,017,849 provides the material in the form of a powder.

The powdered complex, although stable in the dry state, releases the 1-methylcyclopropene when added to water. Release is very quick, typically taking between five and 30 minutes, and complete for small quantities, such as milligrams, of powder. However, 1-methylcyclopropene release from larger quantities of powder can be very slow and incomplete, sometimes taking days. This is especially true for the large quantity of powdered complex needed to treat full-scale fruit storage rooms. Stirring the powder/water mixture does not appreciably speed up 1-methylcyclopropene release when large quantities of the complex are involved.

We have surprisingly found that formulating the 1-methylcyclopropene/α-cyclodextrin powder with carbon dioxide-generating additives such as citric acid and sodium bicarbonate, for example, causes release of 1-methylcyclopropene more efficiently even for large quantities of powder when the powder is contacted with an aqueous solvent. It is very surprising that, even though most of the carbon dioxide itself bubbles off in the first few minutes after water is added to the formulation, actual release of 1-methylcyclopropene occurs slowly in the beginning with the majority of the release 10–60 minutes after addition of water. Continued release occurs as much as 120 minutes after addition of water. Another feature of the formulation is that due to the presence of carbon dioxide hazards associated with the highly flammable 1-methylcyclopropene are reduced.

Effervescent compositions are known. For example, International Patent Application No. WO 98-EP4517 discloses tablets containing. 20 mg piroxicam in as a piroxicam-β-cyclodextrin complex (2:5), sodium glycine carbonate, fumaric acid, PEG 600, spray-dried lactose, lemon flavor, and aspartame. The effervescent tablet allowed higher plasma concentrations 15 minutes after the administration as compared to a standard formulation, as well as a higher drug exposure during the first hours after the administration. However, piroxicam is a high-melting solid; significantly different in properties than the gaseous cyclopropenes of this invention.

Even though this formulation improves 1-methylcyclopropene release dramatically, there is often a need to have the majority of the 1-methylcyclopropene released in less than 120 minutes. This will ensure that the target crop is treated evenly and completely. We have further discovered that the addition of a water soluble substance which itself can complex with the α-cyclodextrin (a "displacing substance") improves 1-methylcyclopropene release even more. Thus, for example, the combination of the 1-methylcyclopropene/α-cyclodextrin complex with citric acid, sodium bicarbonate, and benzoic acid provides very efficient release of 1-methylcyclopropene.

The present invention is, therefore, a composition comprising:

a) a cyclopropene of the formula:

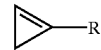

wherein R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;

b) a molecular encapsulation agent within which the cyclopropene is encapsulated; and c) one or more carbon dioxide generating additives; and d) optionally, a displacing substance.

As used herein, the term "alkyl" means both straight and branched chain ($C_1$–$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$–$C_{20}$)alkenyl and ($C_3$–$C_{20}$)alkynyl groups such as, for example, 2-propenyl, 2-butenyl, 3-butenyl, 2-methyl-2-propenyl, and 2-propynyl. The term "cycloalkylalkyl" means a ($C_1$–$C_{15}$) alkyl group substituted with a ($C_3$–$C_6$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means fluorine, chlorine, bromine, and iodine.

Preferably, R is ($C_1$–$C_{10}$) alkyl. More preferably, R is ($C_1$–$C_8$) alkyl. Even more preferably R is ($C_1$–$C_4$) alkyl. Most preferably, R is methyl.

Preferred encapsulating agents include cyclodextrins, crown ethers, polyoxyalkylenes, polysiloxanes, and zeolites.

More preferred encapsulating agents include α-cyclodextrin, β-cyclodextrin, and γ-cyclodextrin. The most preferred encapsulating agent, particularly when the cyclopropene is 1-methylcyclopropene, is α-cyclodextrin. The most preferred encapsulating agent will vary depending upon the size of the R substituent. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

The cyclopropenes applicable to this invention are prepared using the processes disclosed in U.S. Pat. Nos. 5,518, 988 and 6,017,849. The cyclopropene/molecular encapsulation agent complexes of the present invention are prepared by contacting the cyclopropene with a solution or slurry of the molecular encapsulation agent and then isolating the complex, again using general processes disclosed in U.S. Pat. No. 6,017,849.

It is often desirable to include in the composition of this invention one or more adjuvants, such as, for example, binders, lubricants, release agents, surfactants and/or dispersants, wetting agents, spreading agents, dispersing agents, stickers, adhesives, defoamers, thickeners, densifiers, and emulsifying agents. Such adjuvants commonly used in the art can be found in the John W. McCutcheon, Inc. publication *Detergents and Emulsifiers, Annual,* Allured Publishing Company, Ridgewood, N.J., U.S.A. Adjuvants may be added to the composition when formulated or at a later time when the cyclopropene is released.

The composition may be in the form of a free-flowing powder or agglomerated into tablets, wafers, pellets, briquettes, or similar materials. When agglomerated, the composition is preferably pressure agglomerated. A wide variety of pressure agglomeration equipment is available and may be used to agglomerate the composition. These include, for example, presses, granulators, and extruders. Preferred agglomeration equipment are those which are considered high pressure agglomerators such as, for example, pellet presses, tablet presses, and roller presses. Low to medium pressure equipment such as pan granulators or extruders can also be used. However, because they typically require the use of water, to form a slurry, dough, or paste prior to extrusion, uncontrollable and significant loss of the cyclopropene due to desorption from the complex may occur during processing.

Using such pressure agglomeration equipment, the tablets, wafers, pellets, briquettes, and similar forms of agglomerated cyclopropene/encapsulation agent complexes may range from less 0.1 mm in size to more than 5 cm. Preferably the agglomerated material is 0.5 to 2 cm in size. Preferably, the agglomerated material is a tablet or wafer. More preferably, the agglomerated material is a tablet. Optionally, the tablets, wafers, pellets, briquettes, and similar forms of the complexes can be coated with a polymer or other material to delay the onset of release of the 1-methylcyclopropene.

Because cyclodextrins, as well as cyclopropene/cyclodextrin complexes, possess their own tablet binding characteristics, compositions of this invention, in which a cyclodextrin is the molecular encapsulation agent, may be prepared without additional adjuvants. Other encapsulation agents may also possess such inherent binding characteristics.

The 1-methylcyclopropene is released from the compositions of this invention by contacting the composition with water. The temperature of the release water is not critical. Preferably, the release water temperature is from 0 to 90° C.; more preferably from 0 to 70° C.; still more preferably 0 to 50° C.; and most preferably 0 to 35° C. In general, the water is not heated, and is used at ambient temperature. Water to composition weight ratios are preferably between 1:1 and 100:1; more preferably 2:1 to 20:1; and most preferably 3:1 to 15:1.

When α-cyclodextrin is the molecular encapsulation agent, the 1-methylcyclopropene/α-cyclodextrin complex may contain from 0.01 to 5%, by weight, 1-methylcyclopropene; preferably 0.1 to 5%, by weight, more preferably 1 to 5%, by weight.

Preferably the carbon dioxide generating additive is a combination of one or more acids and one or more carbonates or bicarbonates. Preferably, the acid is: citric acid, maleic acid, succinic acid, lactic acid, fumaric acid, tartaric acid, malic acid, adipic acid, p-toluenesulfonic acid, oxalic acid, sulfamic acid, glutaric acid, boric acid, monobasic sodium phosphate, monobasic potassium phosphate, and mixtures thereof. Preferably, the carbonate or bicarbonate is a carbonate or bicarbonate of sodium, ammonium, potassium, calcium, magnesium, or mixtures thereof.

The carbonate or bicarbonate can be in the form of a slow release or a delayed release form made by high pressure agglomeration, a large particle size, or coating the particles with solution delaying substances such as polymer films (see, for example, U.S. Pat. No. 5,674,529).

The displacing substance may be one or more hydrophobic molecules having some water solubility and the ability to complex with the molecular encapsulating agent. When the molecular encapsulating agent is cyclodextrin, for example, benzoic acid, sodium dodecyl sulfate, and various other surfactants, are good displacing substances. The displacing substance may also be one or more water soluble materials such as, for example, dodecyltrimethylammonium chloride, dodecyltrimethylammonium bromide, decyltrimethylammonium chloride, decyltrimethylammonium bromide, and similar quaternary ammonium salts. The displacing substance may be a combination of hydrophobic and water soluble materials. The displacing substance may also be a commercial mixture such as Arquad™ C-33, a quaternary ammonium salt (available from Akzo Nobel).

The composition can take the form of a powder, tablets, pellets, granules, and similar materials.

Thus, typical examples of the compositions of this invention include:

|  | Preferred | More Preferred | Most Preferred |
| --- | --- | --- | --- |
| 1-MCP/α-CD* | 0.1–50** | 0.5–40 | 1–30 |
| Acid | 5–70 | 5–50 | 10–40 |
| Carbonate | 5–70 | 5–50 | 10–40 |
| Displacer | 0–30 | 0.1–20 | 0.5–10 |

*= 1-methylcyclopropene/α-cyclodextrin
**= percent by weight

The 1-methylcyclopropene/molecular encapsulating agent portion can either be mixed intimately with the other additives or kept separate until water is added. Alternately, one or more of the additives may be added to the release water prior to, at the same time, or after the 1-methylcyclopropene/molecular encapsulating agent portion and the release water are contacted with each other.

Preferably, the non-powder (e.g. tablet) compositions of this invention, have a density greater than 1.0, more preferably greater than 1.5, and most preferably greater than 1.7 g/ml.

Some embodiments of this invention are illustrated by the following examples. In these examples, "1-MCP" is 1-methylcyclopropene and "α-CD" is α-cyclodextrin:

EXAMPLE 1
Release of 1-MCP Using Citric Acid and Sodium Bicarbonate Formulation One hundred ml of water was added to a blend of 2.0 grams of a 1-MCP/α-CD complex powder containing 3.3% by weight of 1-MCP, 19.6 g citric acid and 25.8 g sodium bicarbonate in a 1000 ml beaker. This whole system resided in a 36 liter Plexiglas™ airtight chamber fitted with a septum for gas sampling with a syringe. Temperature was 22° C. The chamber was sealed after the water addition and the atmosphere in the chamber was sampled periodically for 1-MCP release. Substantial bubbling lasted 1–3 minutes.

Analysis was by gas chromatography using the following parameters:

| Instrument: | Hewlett Packard (Agilent Technologies) 6890 |
|---|---|
| Detector: | Flame Ionization |
| Detector Temperature: | 150 deg. C. |
| Air Flow Rate: | 450 ml/minute |
| Hydrogen Flow Rate: | 40 ml/minute |
| Make up Gas Flow Rate: | 25 ml/minute |
| Column: | Chrompack CP-PoraPlot Q-HT Dimensions: 10 m × 0.32 mm i.d. Film Thickness: 10 microns |
| Carrier Gas: | Helium |
| Flow Rate: | 2.5 ml/minute |
| Column Head Pressure: | 6 psi |
| Injection Port Temperature: | 150 deg. C. |
| Initial Temperature: | 35 deg. C. |
| Initial Time: | 0.5 minutes |
| Program Rate 1: | 20 deg. C./minute |
| Final Temperature: | 250 deg. C. |
| Final Time: | 6.5 minutes |
| Injection Volume: | 1 ml |
| Injector: | Manual/Splitless (1 ml inlet glass liner) |

As a control, the procedure was repeated with only the 2.0 g of 3.3% 1-MCP/α-CD complex powder, but using a 2 inch magnetic stir bar to mix the suspension and to aid 1-MCP release. Table 1 shows the results. After 2 hours, 64% of the 1-MCP was released with the formulation, but only 18% was released in the stirred control.

TABLE 1

| Time (minutes) | % 1-MCP Released Control (stirred) | % 1-MCP Released Citric acid/sodium bicarbonate, no stirring |
|---|---|---|
| 5 | | 2 |
| 10 | 4 | |
| 20 | | 16 |
| 25 | 6 | |
| 35 | | 30 |
| 50 | | 44 |
| 60 | 9 | |
| 70 | | 53 |
| 90 | 14 | 60 |
| 120 | 18 | 64 |

EXAMPLE 2
Release of 1-MCP Using Citric Acid, Sodium Bicarbonate, and Benzoic Acid Formulation One hundred ml of water was added to a blend of 2.0 grams of a 1-MCP/α-CD complex powder containing 3.3% by weight of 1-MCP, 19.6 g citric acid, 25.8 g sodium bicarbonate, and 5.0 g benzoic acid in a 1000 ml beaker. This whole system resided in a 36 liter Plexiglas™ airtight chamber fitted with a septum for gas sampling with a syringe. Temperature was 22° C. The chamber was sealed after the water addition and the atmosphere in the chamber was sampled periodically 1-MCP release. Substantial bubbling lasted 1–3 minutes. Analysis was by gas chromatography as in Example 1. Table 2 shows the results compared with the previous example containing just citric acid and sodium bicarbonate. After only 80 minutes, the sample containing the benzoic acid had released 100% of the 1-MCP whereas the sample with only citric acid and bicarbonate had only released 50–60% at that point.

TABLE 2

| Time (minutes) | % 1-MCP Released Citric acid/sodium Bicarbonate/Benzoic acid, no stirring | % 1-MCP Released Citric acid/sodium Bicarbonate, no stirring |
|---|---|---|
| 5 | 13 | 2 |
| 20 | 42 | 16 |
| 35 | 65 | 30 |
| 50 | 81 | 44 |
| 65 | 93 | |
| 70 | | 53 |
| 80 | 100 | |
| 90 | | 60 |
| 120 | | 64 |

EXAMPLE 3
Release of 1-MPC Using Citric Acid, Sodium Bicarbonate, and Sodium Dodecyl Sulfate Formulation One hundred ml of water was added to a blend of 2.0 grams of a 1-MCP/α-CD complex powder containing 3.3% by weight of 1-MCP, 19.6 g citric acid, 25.8 g sodium bicarbonate, and 0.5 g sodium dodecyl sulfate (SDS) in a 1000 ml beaker. This whole system resided in a 36 liter Plexiglas™ airtight chamber fitted with a septum for gas sampling with a syringe. Temperature was 22° C. The chamber was sealed after the water addition and the atmosphere in the chamber was sampled periodically for 1-MCP release. Substantial bubbling lasted 1–3 minutes. Analysis was by gas chromatography as in Example 1. Table 3 shows the results compared with Example 1 containing just citric acid and sodium bicarbonate. After 120 minutes, the sample containing the SDS had released 100% of the 1-MCP whereas the sample with only citric acid and bicarbonate had only released 64% at that point. The sample containing SDS did foam considerably more than the control.

TABLE 3

| Time (minutes) | % 1-MCP Released Citric acid/sodium Bicarbonate/SDS no stirring | % 1-MCP Released Citric acid/sodium Bicarbonate, no stirring |
|---|---|---|
| 5 | 9 | 2 |
| 20 | 29 | 16 |
| 25 | | |
| 35 | | 30 |
| 40 | 53 | |
| 50 | | 44 |
| 70 | | 53 |
| 75 | 78 | |
| 90 | 88 | 60 |
| 120 | 100 | 64 |

EXAMPLE 4
Release of 1-MCP Using Citric Acid, Sodium Bicarbonate, and Dextrose Formulation This is an example of using a substance which does not complex well with α-CD as a formulation additive. One hundred ml of water was added to a blend of 2.0 grams of a 1-MCP/α-CD complex powder containing 3.3% by weight of 1-MCP, 19.6 g citric acid, 25.8 g sodium bicarbonate, and 5.0 g dextrose in a 1000 ml beaker. This whole system resided in a 36 liter Plexiglas™ airtight chamber fitted with a septum for gas sampling with a syringe. Temperature was 22° C. The chamber was sealed after the water addition and the atmosphere in the chamber was sampled periodically for 1-MCP release. Substantial bubbling lasted 1–3 minutes. Analysis was by gas chromatography as in Example 1. Table 4 shows the results compared with Example 1 containing just citric acid and sodium bicarbonate. Release for the two systems was very similar, confirming that addition of a molecule which does not complex strongly with α-CD does not have much effect on the 1-MCP release efficiency.

TABLE 4

| Time (minutes) | % 1-MCP Released Citric Acid/Sodium Bicarbonate/Dextrose, no stirring | % 1-MCP Released Citric Acid/Sodium Bicarbonate, no stirring |
|---|---|---|
| 5 | 1 | 2 |
| 20 | | 16 |
| 25 | 14 | |
| 35 | | 30 |
| 45 | 34 | |
| 50 | | 44 |
| 60 | 49 | |
| 70 | | 53 |
| 90 | 63 | 60 |
| 120 | 70 | 64 |

Examples of Various Tablets and Release Solutions
Tablet 1:
  Carbon dioxide generating additive such as, for example, sodium bicarbonate, potassium bicarbonate, sodium carbonate, potassium carbonate, calcium carbonate, or mixtures thereof;
  1-MCP/α-Cyclodextrin complex;
  Optional tableting aids such as binders, lubricants, dispersants, and defoamers;
  Optional soluble densifiers such as sodium chloride, sodium bromide, or Optional insoluble densifiers such as silicon dioxide, zirconium dioxide, or aluminum oxide;
  Optional coating for delayed release.
Tablet 1 release solution:
  Citric, or similar, acid;
  Displacing agent (e.g. dodecyltrimethylammonium chloride, dodecyltrimethylammonium bromide, decyltrimethylammonium chloride, or decyltrimethylammonium bromide;
  Water;
  Optionally defoamer.
Tablet 2:
  Citric, or similar, acid;
  1-MCP/α-Cyclodextrin complex;
  Optional tableting aids and densifiers as above;
  Optional coating.
Tablet 2 release solution:
  Carbon dioxide generating additive such as, for example, sodium bicarbonate, potassium bicarbonate, sodium carbonate, potassium carbonate, calcium carbonate, or mixtures thereof;
  Displacing agent;
  Water;
  Optionally defoamer;
Tablet 3:
  Acid e.g. citric acid;
  Bicarbonate or carbonate e.g. sodium bicarbonate;
  1-MCP/α-Cyclodextrin complex;
  Displacing Agent e.g. dodecyltrimethylammonium chloride;
  Optional tableting aids and densifiers as above;
  Optional coating.
Tablet 3 release solution:
  Water only
Tablet 4—a multilayered tablet containing:
  a) a core comprising a slow release carbon dioxide generating compositon and a shell comprising the composition of Tablet 3; or
  b) an inner layer comprising a slow release carbon dioxide generating additive and an outer layer comprising the composition of Tablet 3.
Tablet 4 release solution:
  Water only In another aspect of this invention are compositions wherein the solid 1-MCP/α-CD is mixed with a solid carbonate or solid bicarbonate or similar material and the carbon dioxide liberating acid is supplied in an aqueous solution.

In yet another aspect of this invention are compositions where the solid 1-MCP/α-CD is mixed with a solid acid etc and the carbon dioxide liberating carbonate or bicarbonate is supplied in an aqueous solution.

We claim:
1. A composition comprising:
   a) a cyclopropene of the formula:

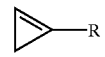

wherein R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;

b) a molecular encapsulation agent within which the cyclopropene is encapsulated; and c) one or more carbon dioxide generating additives.

2. The composition of claim 1, wherein R is $(C_1-C_8)$alkyl.

3. The composition of claim 1, wherein R is methyl.

4. The composition of claim 1, wherein the molecular encapsulation agent is a cyclodextrin or a mixture of cyclodextrins.

5. The composition of claim 1, wherein the molecular encapsulation agent is α-cyclodextrin.

6. The composition of claim 1, wherein the carbon dioxide generating additive is a combination of:

a) one or more acids; and b) one or more carbonates or bicarbonates.

7. The composition of claim 1, further comprising a displacing substance.

8. The composition of claim 7, wherein the displacing substance is benzoic acid, sodium dodecyl sulfate, dodecyltrimethylammonium chloride, dodecyltrimethylammonium bromide, decyltrimethylammonium chloride, decyltrimethylammonium bromide, or a mixture thereof.

9. The composition of claim 1, wherein the composition is in the form of a multilayered tablet.

10. A method for releasing a cyclopropene of the formula:

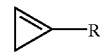

wherein R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;

from a composition comprising:

a) the cyclopropene;

b) a molecular encapsulation agent within which the cyclopropene is encapsulated; and c) one or more carbon dioxide generating additives; comprising the step of contacting the composition with water.

* * * * *